(12) United States Patent
Digiacomantonio et al.

(10) Patent No.: US 8,491,559 B2
(45) Date of Patent: *Jul. 23, 2013

(54) ABSORBENT ARTICLE HAVING A FIT GUIDE

(75) Inventors: Marco Digiacomantonio, Pescara (IT); Evelina Toro, Chieti Scalo (IT); Giovanni Carlucci, Chieti (IT); Remo Bellucci, Spoltore Pescara (IT)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/432,142

(22) Filed: Mar. 28, 2012

(65) Prior Publication Data

US 2012/0238986 A1    Sep. 20, 2012

Related U.S. Application Data

(63) Continuation of application No. 10/852,709, filed on May 24, 2004, now Pat. No. 8,167,862.

(51) Int. Cl.
*A61F 13/15* (2006.01)

(52) U.S. Cl.
USPC .......................................... 604/386

(58) Field of Classification Search
USPC .......... 604/385.101, 386, 387, 389, 391–394, 604/397, 402; 2/80, 113, 236, 239, 400, 403, 2/406
See application file for complete search history.

(56) References Cited

U.S. PATENT DOCUMENTS

| | | |
|---|---|---|
| 4,605,404 A | 8/1986 | Sneider |
| 4,759,754 A | 7/1988 | Korpman |
| 4,911,701 A | 3/1990 | Mavinkurve |
| 4,940,462 A | 7/1990 | Salerno |
| 4,950,264 A | 8/1990 | Osborn |
| 5,344,416 A | 9/1994 | Nihara |
| 5,354,400 A | 10/1994 | Lavash |
| 5,389,094 A | 2/1995 | Lavash |
| 5,429,633 A | 7/1995 | Davis |
| 5,542,941 A | 8/1996 | Morita |
| 5,558,663 A | 9/1996 | Weinberger |
| 5,562,651 A | 10/1996 | Ahr |
| 5,611,790 A | 3/1997 | Osborn |

(Continued)

FOREIGN PATENT DOCUMENTS

| | | |
|---|---|---|
| EP | 0 710 470 B1 | 3/2000 |
| JP | 2003 052743 | 2/2003 |

(Continued)

OTHER PUBLICATIONS

PCT International Search Report dated Sep. 13, 2005.

*Primary Examiner* — Melanie Hand
(74) *Attorney, Agent, or Firm* — Andrew J. Hagerty; Megan C. Hymore

(57) ABSTRACT

An absorbent article having a longitudinal centerline and adapted to be worn in an undergarment having a crotch portion bounded on opposite sides by portions of curved leg openings. The absorbent article comprises a main body portion, the main body portion comprising a liquid pervious body-facing surface, a liquid impervious garment facing surface, and an absorbent core positioned between the body-facing surface and the garment-facing surface. The absorbent article comprises at least one indicator marker visible from the body-facing surface, the indicator markers disposed to indicate proper alignment of the absorbent article with respect to undergarment-specific features such as the curved leg openings.

20 Claims, 11 Drawing Sheets

U.S. PATENT DOCUMENTS

| | | | |
|---|---|---|---|
| 5,650,223 | A | 7/1997 | Weinberger |
| 5,681,303 | A | 10/1997 | Mills |
| 5,704,930 | A | 1/1998 | Lavash |
| 6,682,721 | B2 | 1/2004 | Kim et al. |
| 6,689,344 | B2 | 2/2004 | Chang et al. |
| 6,946,142 | B2 | 9/2005 | Chang et al. |
| 2004/0136927 | A1 | 7/2004 | Kim et al. |
| 2004/0219111 | A1 | 11/2004 | Kim et al. |
| 2005/0031554 | A1 | 2/2005 | Kim et al. |
| 2006/0193793 | A1 | 8/2006 | Kim et al. |
| 2006/0193794 | A1 | 8/2006 | Kim et al. |

FOREIGN PATENT DOCUMENTS

| | | |
|---|---|---|
| JP | 2003 230592 | 8/2003 |
| WO | WO 95/28137 A2 | 10/1995 |
| WO | WO 97/00655 A1 | 1/1997 |
| WO | WO 97/03630 A1 | 2/1997 |
| WO | WO 97/12576 A1 | 4/1997 |
| WO | WO 97/12577 A1 | 4/1997 |
| WO | WO 97/15261 A1 | 5/1997 |
| WO | WO 98/05285 A1 | 2/1998 |
| WO | WO 03/070136 A2 | 8/2003 |

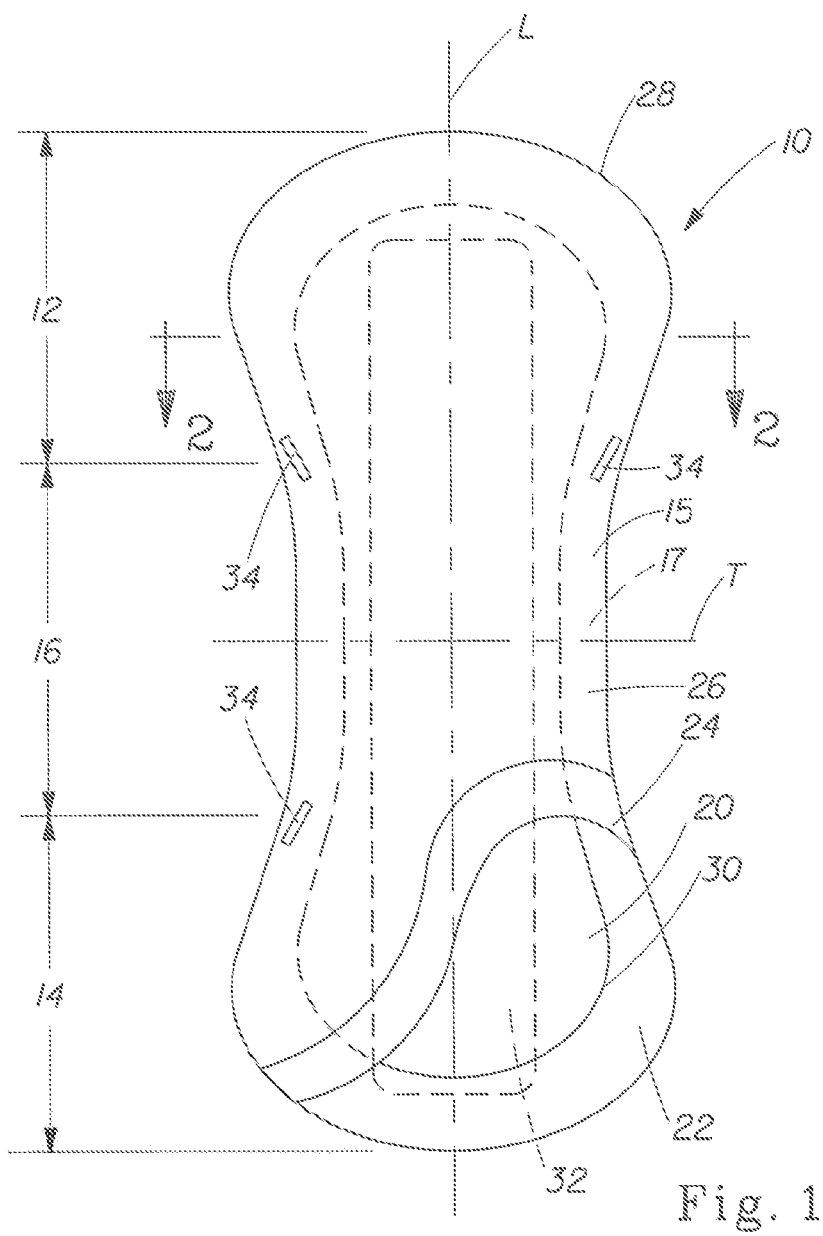
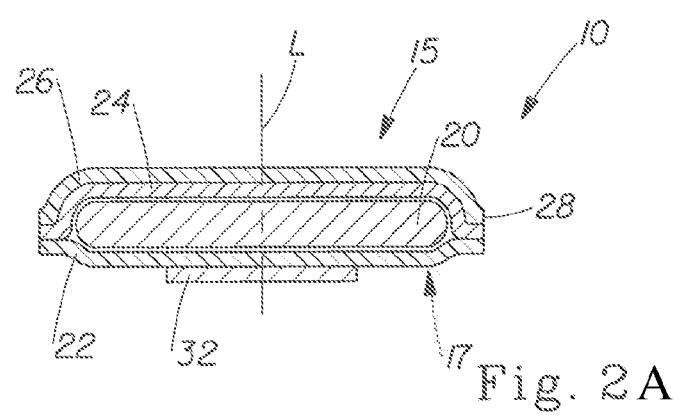
Fig. 1
Fig. 2A

ABSORBENT ARTICLE HAVING A FIT GUIDE

CROSS REFERENCE TO RELATED APPLICATION

This application is a continuation of U.S. application Ser. No. 10/852,709 filed May 24, 2004 now U.S. Pat. No. 8,167,862.

FIELD OF THE INVENTION

The present invention relates to disposable absorbent products, and more particularly to disposable absorbent products intended to be worn in women's undergarments.

BACKGROUND OF THE INVENTION

Sanitary napkins are used by women principally during their menstrual periods to receive and contain menses and other vaginal discharges to protect their garments from soiling. Sanitary napkins typically have adhesive attachment means to temporarily adhere the device to the crotch region of the user's undergarment, normally her panty.

When placing an absorbent article in an undergarment, it is often critical that the article be positioned correctly with respect to the crotch portion thereof. Improper positioning of the absorbent article can result in bodily discharges coming into contact with the wearer's garments or undergarment, instead of entering the absorbent article. For example, if the absorbent article is place to far toward the front of the undergarment, a rearward portion of the undergarment may not be covered by the absorbent article, resulting in fluid, such as menses, soiling the undergarment. The problem is made worse when the absorbent article is asymmetric, such that it does not give a good indication of proper placement, such as absorbent articles that are narrow in the front and wide in the back, or otherwise are not symmetric about a transverse centerline. Further, if the product has what are commonly referred to as "wings" or "flaps" intended to wrap the edges of the wearer's undergarments in the crotch region and/or affix the article to the undergarment, misplacement of the article can result in poor folding and premature detachment.

Changing the size of the absorbent article can help alleviate the problem of improper placement. However, increasing the size, such as the length, of the article also increases the cost, thereby making this solution commercially unattractive.

Accordingly, there remains an unaddressed need for a feminine hygiene article, such as a sanitary napkin or pantiliner, that is designed to facilitate proper placement and positioning in a user's undergarment.

Further, there is an unaddressed need for a means for properly placing and positioning an absorbent article in an undergarment when the absorbent article is not symmetric about a longitudinal and/or transverse centerline thereof.

SUMMARY OF THE INVENTION

An absorbent article having a longitudinal centerline and adapted to be worn in an undergarment having a crotch portion bounded on opposite sides by portions of curved leg openings is disclosed. The absorbent article comprises a main body portion, the main body portion comprising a liquid pervious body-facing surface, a liquid impervious garment facing surface, and an absorbent core positioned between the body-facing surface and the garment-facing surface. The absorbent article comprises at least one indicator marker visible from the body-facing surface, the indicator markers disposed to indicate proper alignment of the absorbent article with respect to undergarment-specific features such as the curved leg openings.

BRIEF DESCRIPTION OF THE DRAWINGS

FIG. 1 is a partially cut away plan view of an absorbent article of the present invention.

FIG. 2A is a cross-sectional view of the section 2-2 as shown in FIG. 1.

DETAILED DESCRIPTION OF THE INVENTION

Figure 3:
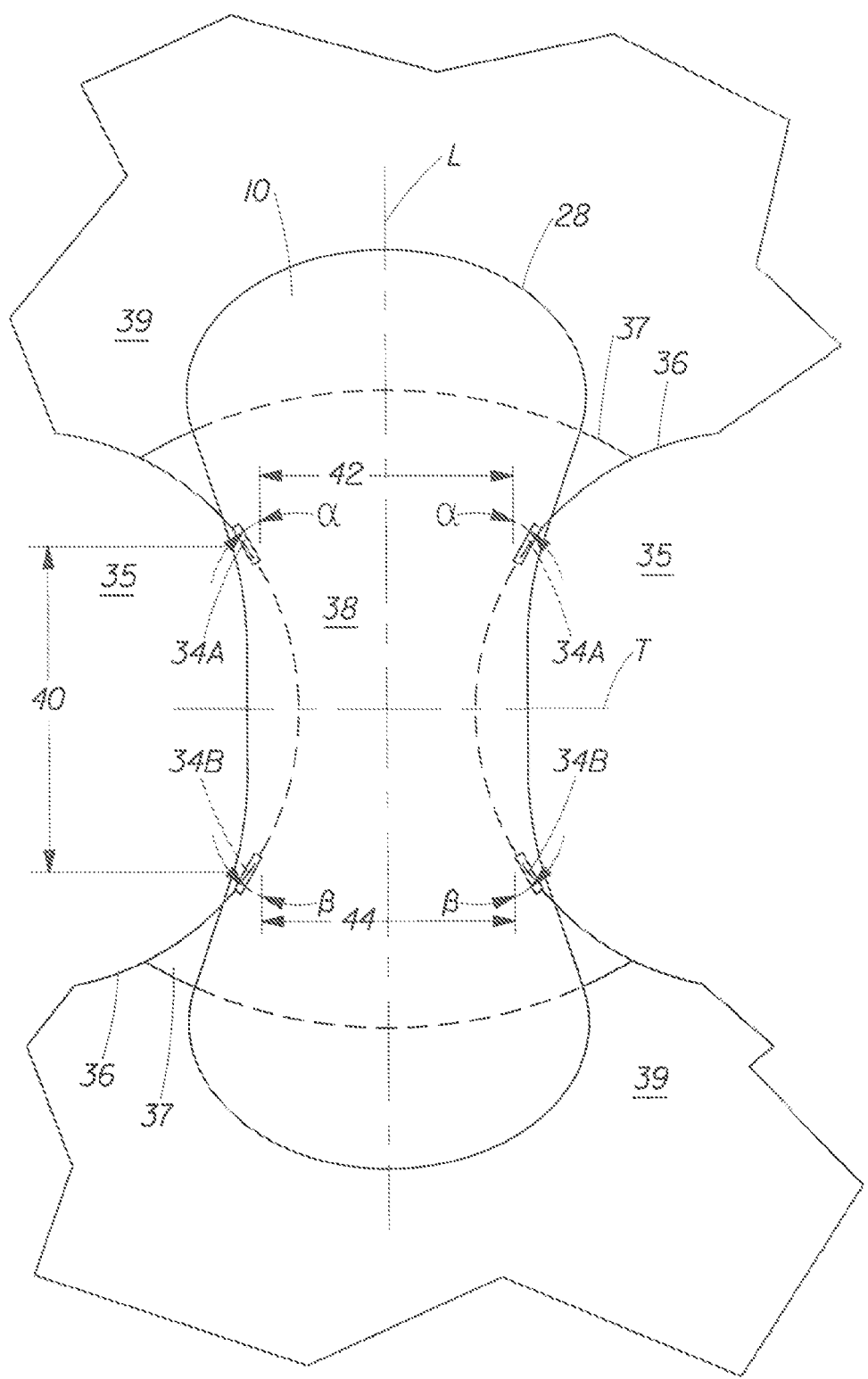
FIG. 3 is a plan view of an absorbent article of the present invention properly positioned in an undergarment.

One embodiment of an absorbent article of the present invention, a sanitary napkin 10, which can be a pantiliner or the like, is shown in partially cut-away plan view in FIG. 1 and in cross section in FIG. 2. A preferred embodiment is a feminine hygiene article, such as a sanitary napkin or pantiliner. While the invention is disclosed in a particularly preferred embodiment of a sanitary napkin, the described invention can also be considered as a pantiliner, and all descriptions below with respect to sanitary napkins can be pantiliners as well, with the difference being one of degree rather than kind. The invention can also be an adult incontinence device, an anal discharge pad, an interlabial pad, or any other absorbent article for which proper placement and positioning in the crotch portion of an undergarment is desirable.

The sanitary napkin 10 has two end regions 12 and 14 and a middle region 16. The sanitary napkin 10 has a body-facing side 15 that is in contact with the user's body and a garment facing 17 side that is in contact with the inner surface of the user' undergarment. In general, each component layer of the sanitary napkin 10 can be said to have a body-facing side and a garment-facing side, the sides being determined by their orientation relative to the use of the article. Sanitary napkin 10 has a longitudinal centerline L and a transverse centerline T that are perpendicular to one another in the plane of the sanitary napkin when in a flat out configuration, as shown in FIG. 1. In one embodiment sanitary napkin is generally symmetric about both longitudinal axis L and transverse axis T. However, in other embodiments, sanitary napkin 10 may be asymmetric about either axis.

While the sanitary napkin 10 may have any shape known in the art, one preferred shape, shown in FIG. 1, is generally "hourglass" shaped, tapering inwardly from a relatively greater transverse width in a portion of one of the end regions to a relatively smaller transverse width at the middle region. Transverse width is generally defined as the dimension across the article, measured parallel to the transverse centerline T. As discussed more fully below, sanitary napkins can also be provided with lateral extensions known commonly in the art as "flaps" or "wings" (not shown in FIG. 1) intended to fold over and cover the panty elastics in the crotch region of the user's undergarment.

Sanitary napkin 10 can have an absorbent core 20 to absorb and store bodily fluids discharged during use. Absorbent core 20 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, a web of polymeric fibers, and a blend of polymeric fibers.

In one embodiment absorbent core 20 can be relatively thin, less than about 2 mm in thickness, preferably less than about 1 mm, and more preferably less than about 0.5 mm in thickness. Thickness can be measured by any means known in the art for doing so. The absorbent core can comprise absorbent gelling materials (AGM), including AGM fibers, as is known in the art.

Absorbent core 20 can be formed or cut to a shape, the outer edges of which define a core periphery 30. The shape of absorbent core 20 can be generally rectangular, circular, oval, elliptical, or the like. Absorbent core 20 can be generally centered with respect to the longitudinal centerline L and transverse centerline T.

To prevent absorbed bodily exudates from contacting the wearer's garments, sanitary napkin 10 can have a liquid impermeable backsheet 22. To provide a degree of softness and vapor permeability for the garment-facing side of sanitary napkin 10, backsheet 22 can be a vapor permeable outer layer on the garment-facing side of the sanitary napkin 20. The backsheet 22 can be formed from any vapor permeable material known in the art. Backsheet 22 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable. A nonwoven web provides for softness and conformability for comfort, and is low noise producing so that movement does not cause unwanted sound.

To provide for softness next to the body, sanitary napkin 10 can have a body-facing layer, referred to herein as topsheet 26. Topsheet 26 can be formed from any soft, smooth, compliant, porous material which is comfortable against human skin and through which fluids such as vaginal discharges can pass. Topsheet 26 can comprise fibrous nonwoven webs and can comprise fibers as are known in the art, including bicomponent and shaped fibers. Topsheet 26 can also be a liquid permeable polymer film, such as an apertured film, or an apertured formed film as is known on sanitary napkins such as ALWAYS® brand sanitary napkins.

At least one, and preferably both, of topsheet 26 and backsheet 22 define a shape, the edge of which defines an outer periphery 28 of the sanitary napkin. In a preferred embodiment, both topsheet 26 and backsheet 22 define the sanitary napkin outer periphery 28. The two layers can be die cut, as is known in the art, for example, after combining all the components into the structure of the sanitary napkin as described herein.

Interposed between the absorbent core 20 and topsheet 26 can be a fluid permeable secondary topsheet 24. Secondary topsheet 24 can aid in rapid acquisition and/or distribution of fluid and is preferably in fluid communication with the absorbent core 20. In one embodiment, the secondary topsheet 24 does not completely cover the absorbent core 20, but it can extend to core periphery 30.

In one embodiment, absorbent core 20 does not extend laterally outward to the same extent as either topsheet 26 or backsheet 22, but the sanitary napkin outer periphery 28 can be substantially larger than the core outer periphery 30. In this manner, the region of sanitary napkin 10 between the core periphery 30 and the sanitary napkin outer periphery 28 can define a breathable zone 32 that permits vapors to go through portions of the sanitary napkin, thereby escaping and providing for dryer comfort when worn. The breathable zone and sanitary napkin having a breathable zone can be according to the teachings of U.S. patent application Ser. No. 10/790,418, filed Mar. 1, 2004.

All the components can be adhered together with adhesives, including hot melt adhesives, as is known in the art. The adhesive can be Findlay H2128 UN and Savare' PM 17 can be applied using Dynafiber HTW system.

As is typical for sanitary napkins and the like, the sanitary napkin 10 of the present invention can have panty fastening adhesive 32 disposed on the garment-facing side 17 of backsheet 22. Panty fastening adhesive 32 can be any of known adhesives used in the art for this purpose, and can be covered prior to use by a release paper, as is well known in the art.

The above disclosure is meant to give a general description of the basic parts of feminine hygiene articles such as sanitary napkins and the like as they are known in the art. The description is not intended to be limiting. Any and all of various known elements, features and processes of known sanitary napkins, pantiliners, incontinence pads, and the like can be incorporated in an absorbent article of the present invention as desired or needed for particular use benefits. Now, with respect to the remaining disclosure, the novel features and benefits of the present invention will be described.

As shown in FIG. 1, an absorbent article of the present invention has at least one indicator marker 34 visible from the body-facing surface 15. The indicator markers 34 provide an indication for proper fit when placing and positioning the sanitary napkin 10 in an undergarment, such as the panty of the wearer. Indicator markers 34 can comprise printed indicia, such as ink-jet printed lines or line segments, embossed ridges or bumps, folds, pleats, or any other means known in the art for providing visible indications that serve the function of being indicator markers 34, which is to aid the user in determining proper placement of the article in an undergarment. Specifically, as shown in FIG. 3, indicator markers 34 can be disposed so as to indicate proper placement of the absorbent article with respect to undergarment-specific features such as an undergarment 39. For example, the crotch portion 38 of the undergarment 39 can have seams 37 associated therewith, and is bounded on opposite sides by elasticized leg elastics 36 of the curved leg openings 35.

Indicator markers 34 can be disposed to be visible from the body-facing surface 15 such that an indication is made to the user as to the proper positioning in the undergarment. Undergarments typically have undergarment-specific features such as sewn seams, hemmed edges, elasticized leg openings, additional crotch panel material, and other visibly-distinct portions that can be used for alignment with indicator markers 34. Therefore, in some embodiments of the present invention, indicator markers 34 can be disposed so as to indicate alignment with a sewn seam, such as seam 37 of a crotch panel of the panty of the wearer. A crotch panel can be, for example, an additional piece of cotton material sewn into the crotch portion 38 of a panty-style undergarment 39. However, in a preferred embodiment, indicator markers 34 are disposed to indicate alignment and fit of a sanitary napkin with respect to the leg elastics 36 of the undergarment, as discussed more fully below.

FIG. 3 shows a sanitary napkin 10 outer periphery 28 as seen when properly positioned in the crotch portion 38 of a panty 39. Sanitary napkin 10 shown in FIG. 3 is an example of an article of the present invention not having flaps intended to wrap the edges of the leg openings of the undergarment. As shown in FIG. 3, portions of the panty 39 defining leg openings 35, such as leg elastics 36, can be positioned under a portion of sanitary napkin 10 when the sanitary napkin 10 is properly placed in the crotch region 38 of the panty. To aid in placing and positioning the sanitary napkin 10 properly, in one embodiment indicator markers 34 can be disposed so as to indicate proper alignment of the absorbent article 10 with respect to the curvature of leg openings 35 of the undergarment 39.

As shown in FIG. 3, indicator markers 34 can be placed so as to give the user a visual indication of proper placement of the article in the undergarment. Because the actual curvature of leg elastics in panty leg openings can be asymmetric about the transverse axis T of the article 10, in one embodiment indicator markers 34 can differ in size and orientation based on their location with respect to the panty leg opening. For example, in FIG. 3, indicator markers 34A can be associated with the forward or "front" portion of the leg openings (that is, the portion of the leg openings more toward the front of the wearer). Likewise, indicator markers 34B can be associated with the rearward or "back" portion of the leg openings.

Undergarment styles can differ greatly, and the style of undergarment, such as panties, can have an impact on the curvature of the leg openings 35 bounding the crotch portion 38 of the undergarment. For this reason, absorbent articles, such as sanitary napkin 10, can be designed for various panty sizes by varying the disposition of indicator markers 34 in a lengthwise direction as indicated by dimension 40 on FIG. 3, and in a widthwise direction, as indicated by dimensions 42 and 44 on FIG. 3. Dimensions 42 and 44 can be different or substantially the same. Dimensions 42 and 44 can be measured in any convenient way, such as from "inside-to-inside" (least dimension between marks, measured laterally parallel to transverse centerline T) or "outside to outside" (greatest dimension including marks measured laterally parallel to transverse centerline T) or from "center to center" as is most appropriate for the type of indicator marker. In one embodiment, a minimum dimension measured inside-to-inside can be 20 mm, and a maximum dimension measured inside-to-inside can be 85 mm, and the inside-to-inside dimension can be any measurement of increments of 1 mm between the minimum and maximum. For "thong" type panties, for example, it may be desirable to have indicator markers 34B separated by the minimum inside-to-inside dimension of about 20 mm.

In one embodiment indicator markers 34 are generally elongated in shape, and can be generally linear or have a slight curvature. For example, as shown in FIG. 3, indicator markers 34 can be generally linear-shaped rectangular marks or line segments. Indicator marks 34 can be made by printing, stamping, embossing, folding or any other known process that makes a visual, or even tactile, impression that indicates proper alignment for the user. In the case of generally linear marks, such marks can make an angle with respect to the longitudinal centerline L. The angle can be the same for all indicator marks, or different angles can be used for the forward indicator marks 34A and rearward indicator marks 34B. As shown in FIG. 3, forward indicator markers 34A can be oriented at an angle α, and rearward indicator markers 34B can be oriented at an angle β from the longitudinal centerline L. As used herein all angle measurements are taken as being positive and increasing away from a line parallel to the longitudinal centerline L and having a vertex oriented nearer the transverse centerline T. Angle α can be oriented in a range in 1 degree intervals from about 5 degrees to about 45 degrees. Likewise, angle β can be oriented in a range in 1 degree intervals from about 5 degrees to about 45 degrees.

The indicator markers 34 of the present invention are particularly beneficial when incorporated on an absorbent article that is asymmetric about either of the transverse centerline T or longitudinal centerline L, and/or an absorbent article that incorporates flaps for folding about the leg elastics 36 of the undergarment 39.

Figure 4:
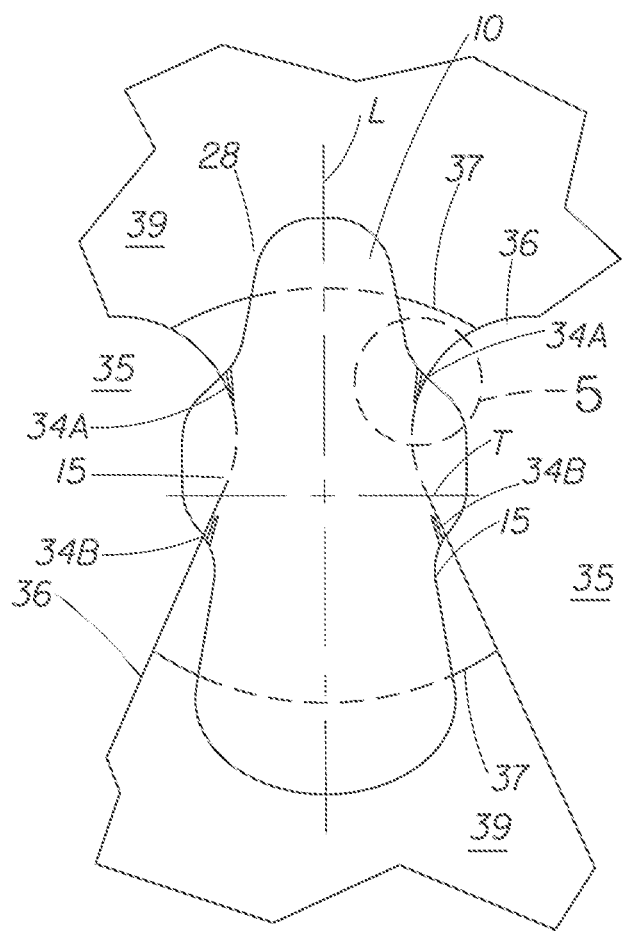
FIG. 4 is a plan view of another embodiment of an absorbent article of the present invention properly positioned in an undergarment.

FIG. 4 shows a sanitary napkin 10 having flaps 15 that are intended to fold over and wrap the leg elastics (flaps 15 in FIG. 4 are shown in an unfolded, flat condition). Flaps 15 can have attachment means (not shown) to affix the sanitary napkin to the underside of the undergarment, as is known in the art. Any of various attachment means known in the art can be used with the present invention, including pressure sensitive adhesive means, in which case release strips can be incorporated as well. It is known to make a line of weakness or a flexible zone to facilitate folding of flaps on sanitary napkins. However, such fold lines are not to be confused with the indicator markers 34 of the present invention. Whereas fold lines (if noticeable at all by the consumer) are simply made to permit folding around a wide range of panty sizes and styles, they are not necessarily sufficiently shaped, placed, or otherwise designed to be fit guides for proper placement and positioning. Therefore, since they permit incorrect placement and positioning of the sanitary napkin, they are not indicator markers 34. In some embodiments, indicator markers 34 of the present invention can be in addition to and distinguished over flap fold lines. That is, indicator markers 34 can be visually or tactilely distinct over any fold lines for flaps.

FIG. 4 also illustrates a sanitary napkin 10 that is asymmetric about the transverse centerline T. One way of describing such a sanitary napkin 10 is to say that one of the end regions 12 or 14 is longer in a dimension parallel to the longitudinal centerline L than the other. Such a sanitary napkin, when properly placed in an undergarment can result in more of the absorbent capacity toward the rear of the user's undergarment for better protection from soiling. In general, a central region 16 is designed to be placed in the narrowest portion of the crotch region of a user's undergarment. However, asymmetric designs present a problem to the user. Because the pad is not designed for the transverse centerline T to be in the center of the crotch region 38, the user can very easily mis-position the article in her undergarment. In general, it has been found that for asymmetric sanitary napkins of the type illustrated in FIG. 4, users typically position the article too far forward in their undergarment. This is believed due to force of habit since users typically place absorbent articles such that the pad is generally centered with respect to the central portion of the crotch of the undergarment. Such misplacement has been shown to have a direct correlation to reduced fit, reduced comfort, and increased soiling conditions, such as spotting of the user's undergarments.

Figure 5:
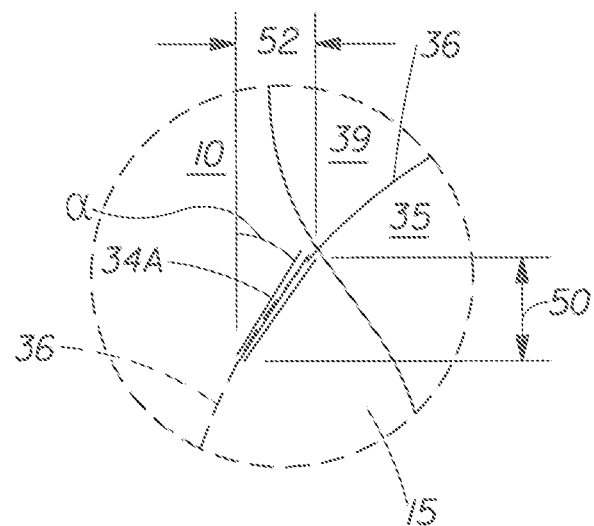
FIG. 5 is an enlarged detail view of an indicator marker of the present invention.

The indicator markers 34 of the present invention aid in proper placement by giving the user a visual signal of proper positioning with respect to the crotch portion of the undergarment. Especially for asymmetrical sanitary napkins, such a visual signal has been found to greatly increase the frequency of proper placement among sanitary pad users. As shown in FIG. 4, and more clearly in the enlarged portion shown in FIG. 5, indicator markers 34 can be on the sanitary napkin 10 to indicate proper positioning with respect to the curvature of leg elastics 36. Each indicator marker 34 can comprise a plurality of linear indicators, such as the three line segments shown in FIGS. 4 and 5, and the plurality of linear indicators can be generally parallel to one another, or they can be non-parallel, as shown in FIG. 5. When individual marks of an indicator marker 34 are non-parallel, each mark can be oriented at an angle that is greater in proportion to an increased distance measured from the longitudinal centerline L. In such a case, the angle α for the plurality of marks can be considered to be the average of the angles for a given plurality of indicator marks making up one indicator marker 34.

As shown in FIG. 5, indicator marker 34A (and, in general indicator markers 34) can be a single mark (or embossment, fold, pleat, and the like) or a plurality of individual marks. In either case, indicator marker 34 can be measured and quantified in at least two ways. As shown in FIG. 5, indicator marker 34 can have a length dimension, indicated as 50 and a width dimension indicated as 52. These dimensions, measured to the extremities of indicator marker 34 (including individual marks, if necessary) parallel to the longitudinal centerline L and the transverse centerline T, respectively, define an angle α (or β for rearward indicator markers 34B) and a ratio R1 of length 50/width 52 which is defined as 1/tan α. For non-parallel, "fanned-out" marks (or pleats, etc.), as shown in FIG. 5, angle α can correspond to an intermediate angle, such as an average angle of all the marks. In one embodiment, the ratio R1 can be greater than 1, and can be greater than 2, 3, 4, 5, 10, 15, or more. In general, the angle α necessary for proper fit guidance will be determined by the size of the article, its symmetry about either of the longitudinal or transverse axes, and the type and size of undergarment for which it is designed. It has been found that an angle α (or β for rearward indicator markers 34B) of between about 10 degrees to about 30 degrees, variable in 1 degree increments, is sufficient. In one embodiment having "fanned-out" marks (or pleats, etc.), as shown in FIG. 5, angles α or β can vary for each individual mark from between about 10 degrees to about 30 degrees.

Figure 6A:
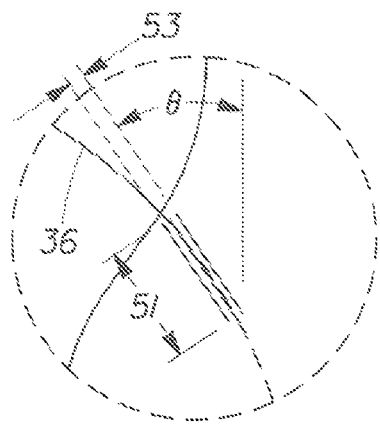
FIG. 6A is an enlarged view of the highlighted portion in FIG. 6.
Figure 6:
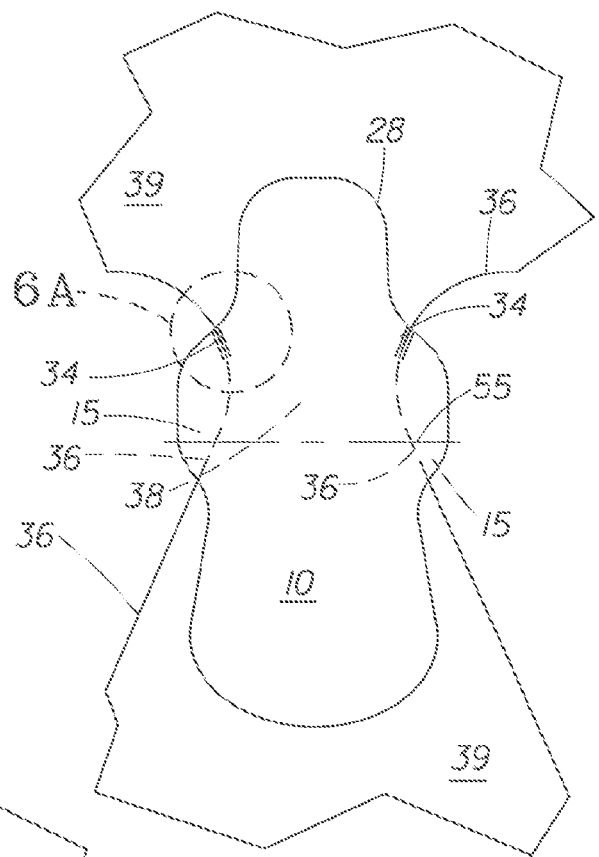
FIG. 6 is a partial plan view of a properly aligned absorbent article of the present invention.

A second way of quantifying the configuration of indicator markers 34 is shown with respect to FIGS. 6 and 6A. As shown, an effective length dimension, indicated as 51 and an effective width dimension indicated as 53. Measured in this manner, a second ratio R2 of dimension 51/dimension 53 can be defined. Defining ratio R2 permits the indicator marker 34 to be specified by ratio R2 and an independently-determined angle Θ. In general, ratio R2 can be greater than 1, and can be greater than 2, 3, 4, or 5. Angle Θ can be at least about 10 degrees measured relative to a line parallel to longitudinal centerline L, and the first laterally-outboard mark (or pleat) of indicator marker 34, as shown in FIG. 6A. Angle Θ can be at least about 15 degrees, at least about 20 degrees, at least about 25 degrees, and at least about 30 degrees. Preferably angle Θ is less than about 45 degrees.

In general, it has been found that indicator markers 34 having a relatively high ratio R1 or R2 of about 2 to 5, and a relatively low angle α or β or Θ of between about 10 degrees to about 30 degrees, provides for an absorbent article having indicator markers 34 suitable for a wide range of panty sizes. If a plurality of angled marks is used, such as shown in FIGS. 5 and 6, it is desirable that the minimum and maximum angles (α or β or Θ) fall within the range of about 15-30 degrees for forward indicator markers 34A, and in the range of about 10-20 degrees for rearward indicator markers 34B. In general, the placement of indicator markers 34, including with respect to a length dimension 40 or width dimensions 42 or 44, can be varied to correlate to predetermined panty sizes.

Figure 7:
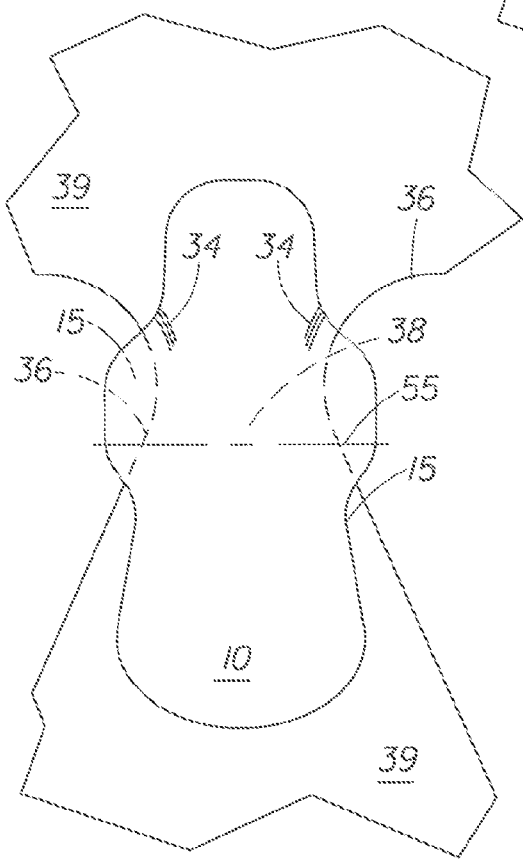
FIG. 7 is a partial plan view of an improperly aligned absorbent article of the present invention.

As shown in FIGS. 6 and 7, indicator markers 34 can serve as a fit guide to properly position a sanitary napkin 10 in an undergarment by indicating proper alignment with respect to leg elastics 36. As shown in FIG. 6, a properly positioned sanitary napkin 10 aligns indicator markers 34 with leg elastics 36 where the leg elastics 36 intersect sanitary napkin periphery 28. In this manner, by visual signal, the user can properly position the sanitary napkin 10 with respect to the crotch portion 38 of the undergarment 39, for example, a lateral section 55 of the crotch portion 38 of the undergarment 39. If sanitary napkin 10 is improperly positioned, for example positioned too far forward as shown in FIG. 7, indicator markers 34 no longer align with leg elastics 36. The user, noticing the mis-alignment, can then re-align the sanitary napkin if necessary. By having indicator markers 36 comprised of a plurality of marks or folds, a range of proper placement can be provided for, thereby permitting a sanitary napkin to fit a range of undergarment sizes and types.

As indicated in FIGS. 6 and 7 as well, it is not necessary that sanitary napkin 10 comprise both forward and rearward indicator markers 34A and 34B. In practice, only forward or rearward indicator markers are necessary. In fact, a workable sanitary napkin need only have one indicator marker 34, for example one of the left or right of either forward or rearward indicator markers 34A and 34B. However, having more than one mark is believed to make positioning easier for the user.

As shown in FIGS. 8-11, indicator markers 34 can be printed on a surface visible from the body-facing surface of sanitary napkin 10. The indicator markers 34 can be printed on a surface below the topsheet as long as it is visible to the user during placement and positioning of the article in the undergarment. Therefore, indicator markers 34 can be printed, or otherwise disposed on, secondary topsheets, surge layers, acquisition layers, absorbent cores, and the like. Indicator markers 34 can be configured as lines, line segments, curved lines, bands, arrows, words, pictures, or any other printed indicia having a purpose of providing a fit guide indication. Again, the visual indicia need not be printed on the body-contacting surface, but need only be visible from the body-contacting surface such that the user can see the indicator marks 34 as she places the sanitary napkin 10 in her undergarment 39.

Figure 8:
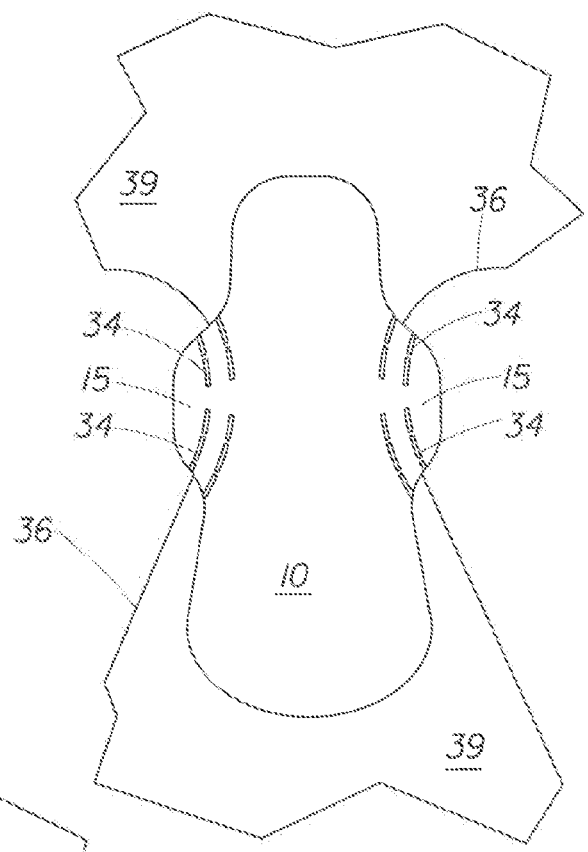
FIGS. 8-21 illustrate various alternative embodiments of sanitary napkins having indicator markers of the present invention.
Figure 9:
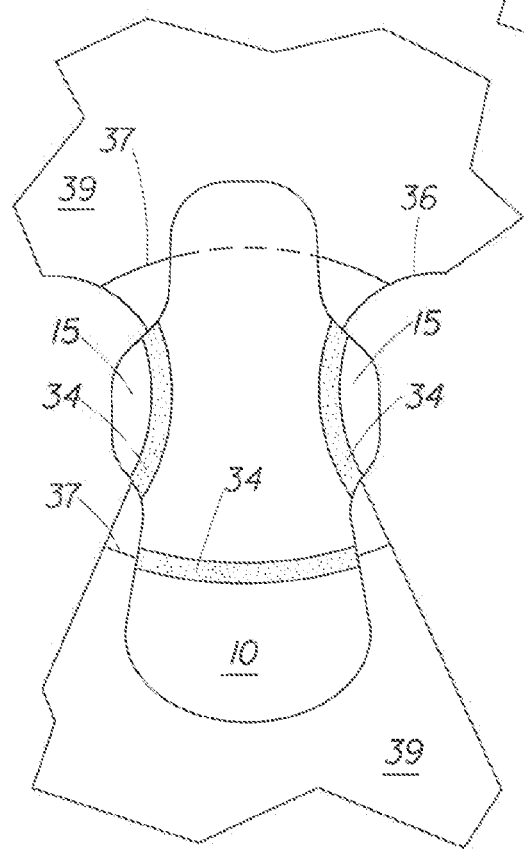

As shown in FIGS. 8 and 9, indicator markers 34 can provide an indication of where the undergarment elastic should go by giving a visual representation of where the elastic should be underneath the article. FIG. 9 shows an embodiment in which an indicator marker 34 is disposed to overlie a seam 37 of the undergarment, such as a seam of a sewn-in crotch panel. Indicator marker 34 overlying seam 37 can be used alone, or in combination with other indicator markers 34 as shown in FIG. 9.

Figure 10:
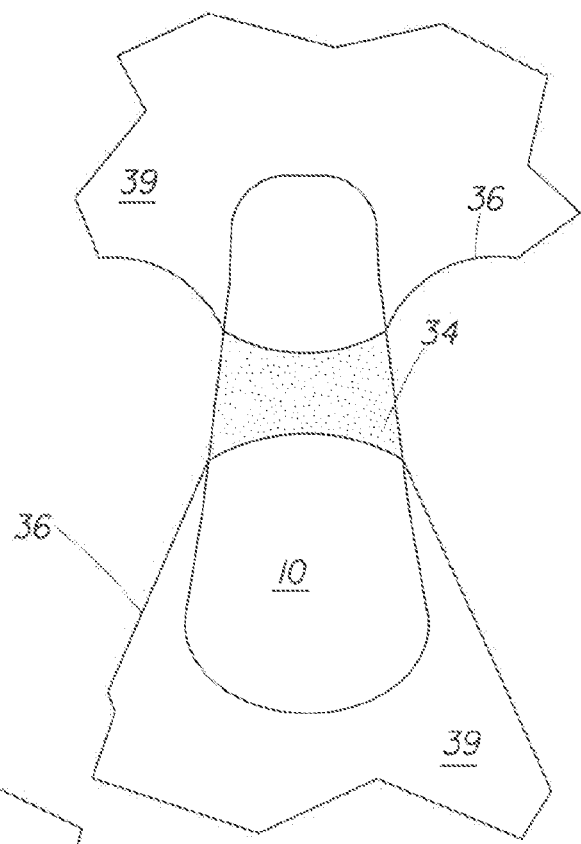

FIG. 10 shows an embodiment in which one continuous indicator marker 34 can provide an indication at all four locations that leg elastics 36 go under the sanitary napkin 10, resulting in the benefit of proper fit. The indicator marker 34 of FIG. 10 can be a solid colored band that extends across the entire article, including the flaps, if utilized. Alternatively, indicator marker 34 of FIG. 10 can be a shaded, striped, stippled, or other noncontiguous band that gives the impression of being a continuous colored band. In one embodiment, the "corners" of the band as shown in FIG. 10 can line up with the edges of the article which cross over the leg elastics 36 of undergarment 39.

Figure 11:
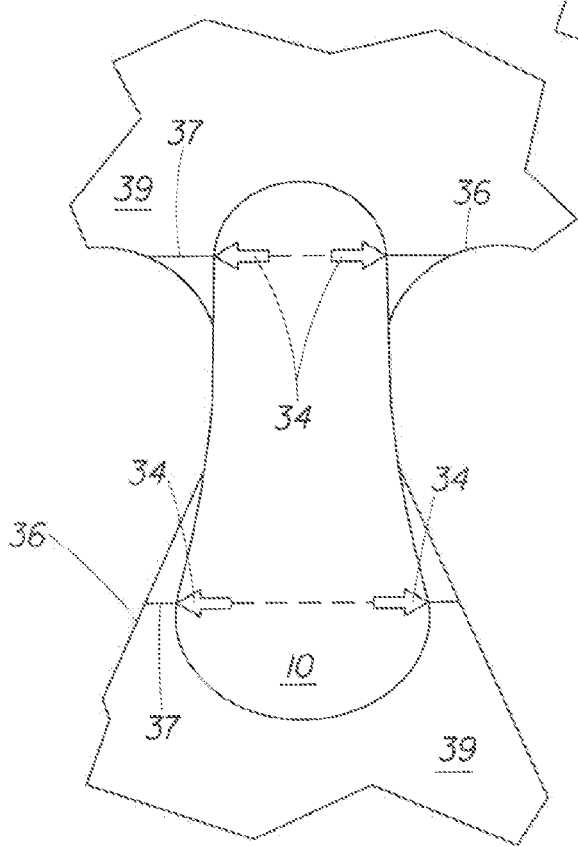

FIG. 11 shows an embodiment in which printed arrows indicate the points at which seams 37 should cross under the article 10. In one embodiment, multiple indicator markers 36 can be utilized and appropriately marked to convey fit for various sized undergarments.

Rather than utilize printed-on marks for indicator markers 34, the article of the present invention can utilize other visual or tactile indicia. For example, indicator markers 34 can be differentially extensible zones on flaps 15 as taught in WO 97/12577, issued 10 Apr. 1997 to Lash et al.; or WO 96/12461, issued 19 Oct. 1995 to Gellich et al. Differentially extensible zones are formed by mechanically straining portions of the sanitary napkin to permanently stretch and deform ridges and valleys. Such straining can be by the method commonly referred to as ring-rolling, or strained areas can be local stainable networks made by what is referred to in the art as SELF'ing. However, these embodiments show extensible zones having configurations that are not suited for use as indicator markers 34 of the present invention. In general, the deformed regions suitable for extensible zones extend to far laterally-outward into the wing area, thereby not providing for reliable fit guides.

Even though deformed regions modified to be indicator markers 34 can be extensible zones that aid in wrapping and conforming the wing about the leg elastics in the crotch region of an undergarment, it is clear that the indicator markers 34 need not perform the function of stretch or extension to aid in wrapping the flaps to better conform to the undergarment. They simply need to provide a visual indication of proper fit, such as having the ridges being properly angled and of a sufficient length to align with the panty elastics when worn in an undergarment of the appropriate size.

Figures 12, 13:
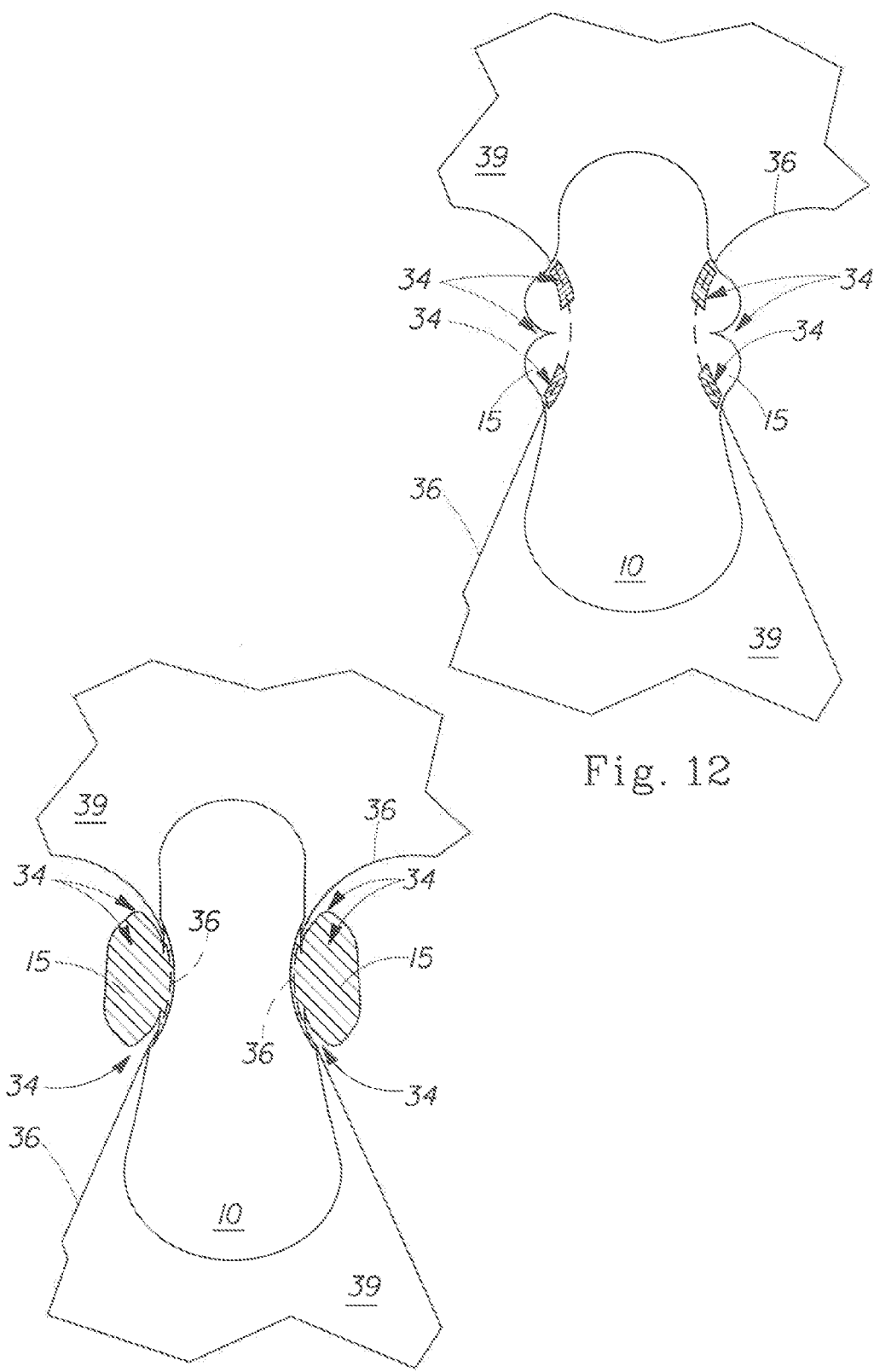

Aside from printed marks, other indicator markers 34 can be utilized. For example, as shown in FIGS. 12 and 13, notches or indentations can be utilized in conjunction with other indicator markers 34. In FIG. 12, notches in flaps 15 can indicate by "pointing," for example, to where the center of the crotch portion 38 of undergarment 39 should be with respect to sanitary napkin 10. Such a pointer can reinforce in the users mind the correct placement as indicated by, for example, printed indicator marks 34 to mark the cross-over point with the panty elastics 36. In FIG. 13, notches at the base of flaps 15 can function together with a printed-on indication in the wings 15 as indicator markers 34 by giving the user an indication of where leg elastics 36 should be disposed with respect to sanitary napkin 10.

Figure 14:
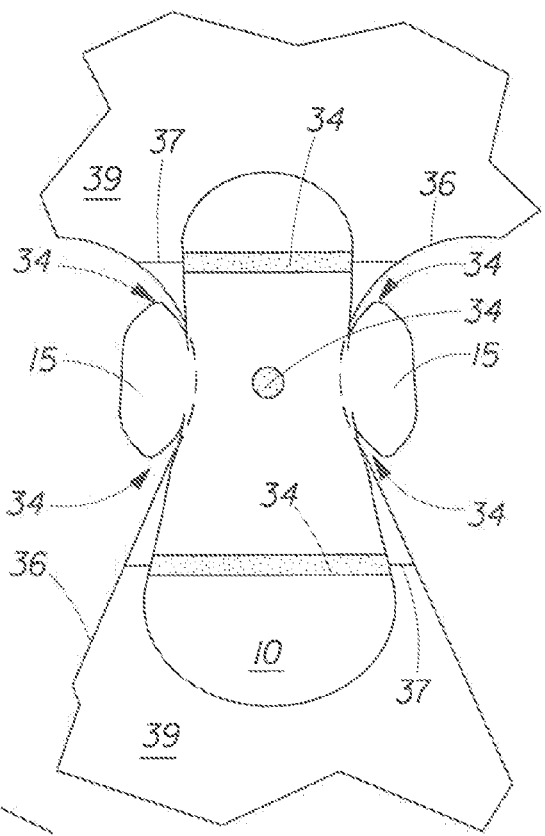

Other embodiments, for example, a combination of a centrally-printed mark, seam-indicator marks, and notches, as shown in FIG. 14 can be utilized. As shown in FIG. 14, a centrally-placed marking, such as a shaded circular shape, can act as an indicator marker 34, and can be utilized alone or together with other indicator markers, as shown.

Figure 15:
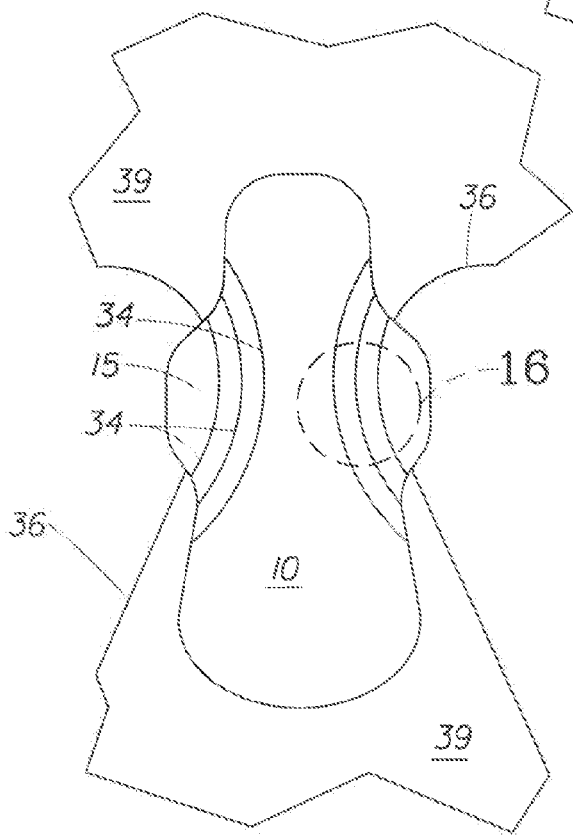
Figure 16:
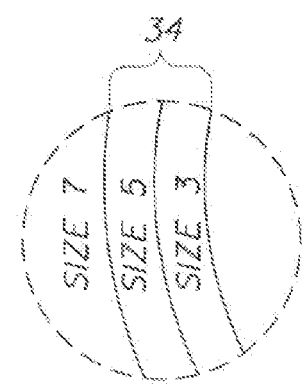

FIG. 15 shows an embodiment using printed indicia in the form of lines, words and numbers. In this embodiment a series of lines of indicator markers 34 can be provided that correspond to typical shapes of leg openings and crotch widths for various sizes of undergarments. Even if the user's undergarment does not match exactly to the indicator markers 34 provided, such a configuration provides a visual signal of the central region of the absorbent pad anyway, and can be used to place such a central region properly with respect to the crotch portion 38 of an undergarment 39.

Figure 17:
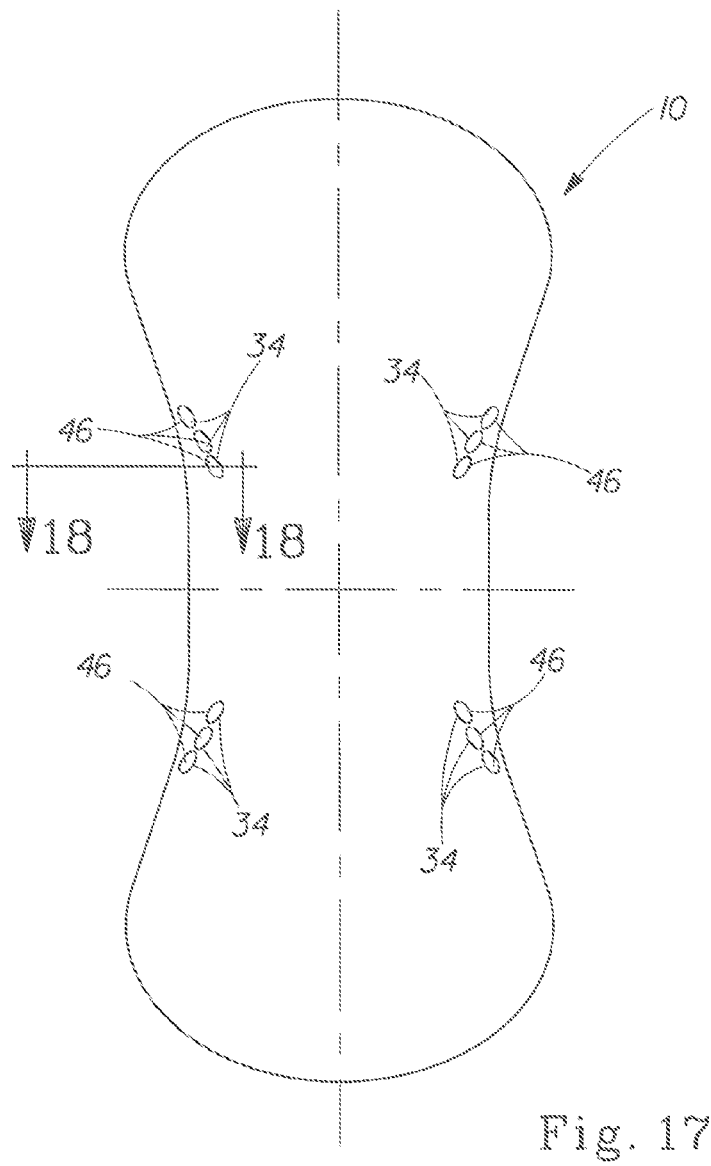
Figure 18:
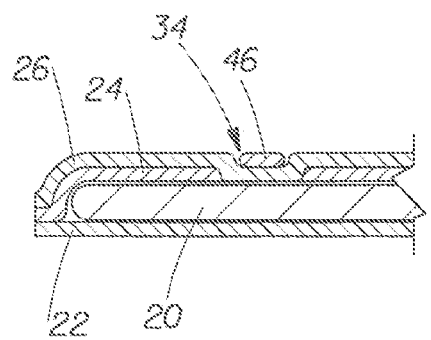

FIGS. 17 and 18 illustrate another embodiment of the present invention combining embossing and printing or other methods known in the art for imparting color, to make indicator markers 34. As shown in FIG. 17, sanitary napkin 10 can comprise indicator markers 34 comprising a plurality of embossments that together form a generally linear indicator mark 34. As shown in FIG. 18, one or more of the embossed impressions, preferably all the embossed depressions can have therein a visible color 46. The visible color can be printed in registration with the embossments, or printed at the same time as the embossments are made. The color 46 can be due to printing inks or colored adhesive. The color 46 can also be under the topsheet, even on a separate layer (neither shown in FIG. 18), such that upon embossing, color 46 shows through the embossed portion, thereby giving the appearance of having been printed in registration with the embossed indicator marker 34.

Figure 19:
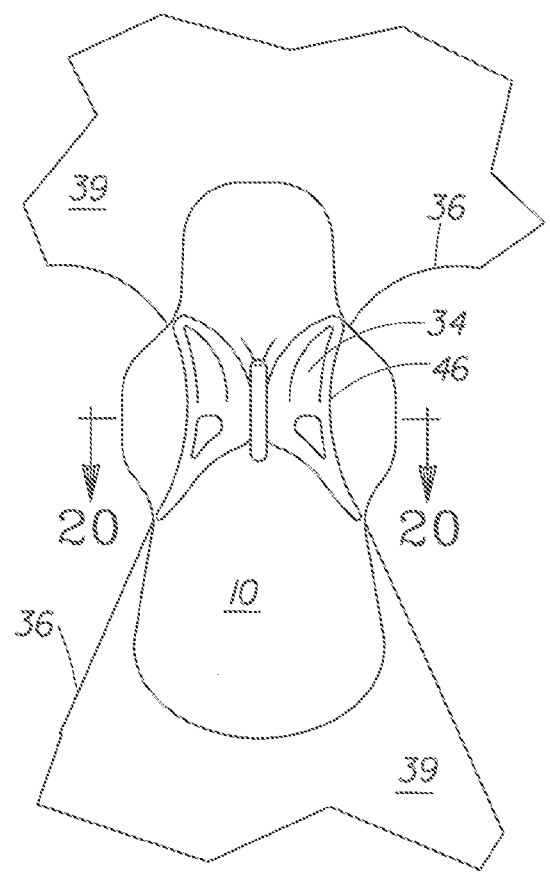
Figure 20:
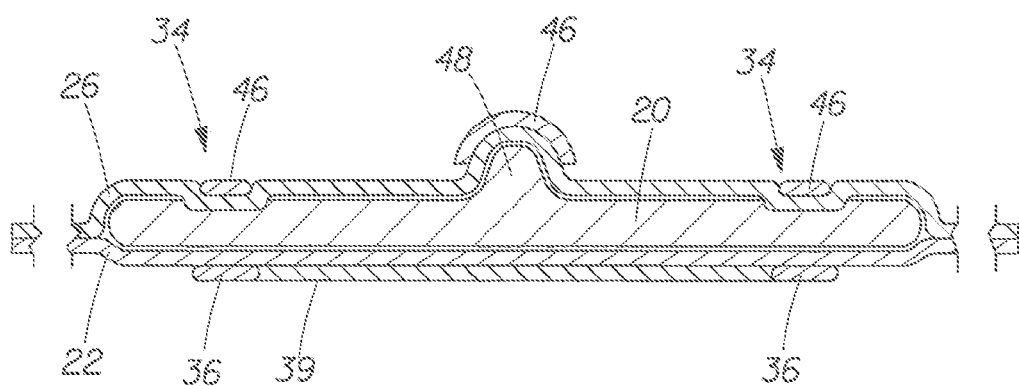

FIGS. 19 and 20 illustrate a further embodiment in which printing and embossment are utilized together. As shown in FIG. 19, indicator marker 34 can be a recognizable image, such as a butterfly, the image having components that indicate fit, such as the tips of the butterfly wings that coincide with the intersection of the sanitary napkin 10 and leg elastics 36. As shown in FIG. 20, certain features of the image can be colored by printing visible colored portions 46 in a printed image that can be enhanced by embossing (as in the wings in the illustrated embodiment), or by debossing (i.e., creating raised portions, as in the body of the butterfly in the illustrated embodiment). As discussed with respect to FIGS. 17 and 18, the colored portions 46, made by printing or other methods known in the art for imparting color, can be registered with embossed or debossed regions to give a synergistic image of indicator markers 34 useful as a fit guide in a disposable absorbent article.

The embossed and debossed portions of the fit guide can provide a tactile impression that can be used as a fit guide as well. For example, the user can gently touch the edges of the sanitary napkin and follow the line of an embossment, for example, while visually comprehending that the leg elastic 36 follows the felt path of her finger. In a separate but related benefit, the debossed, or raised portion of an image such as the butterfly in FIG. 19 can aid in assessing proper fit by providing to the user a tactilely evident positioning guide. The raised portion can be made, for example, to fit over or in the labial region of the wearer's anatomy, and misplacement can be immediately detected upon pulling the undergarment into place.

In another embodiment, a fit guide can be achieved by having indicator markers that are only tactilely sensed, i.e., not visibly sensed. Such a tactile fit guide can serve as an indicator marker 34 by means of a change in surface smoothness, a change in the coefficient of friction, or other tactilely-sensed change in material properties. In general, the change in material properties can correspond in location to the visible indicator markers 34 as disclosed herein.

In another embodiment, fit guide can be achieved by having indicator markers 34 that indicate by means of variations in the bending stiffness of flaps 15 on sanitary napkin 10. In this embodiment, the regions indicated in previously-disclosed embodiments corresponding to indicator markers 34 can have a relatively lower resistance to bending about the leg elastics 36 of the undergarment 39. Upon attempting to fold the flaps over the crotch portion of the undergarment, the user can feel resistance to bending when the sanitary napkin is not positioned correctly within the undergarment. For example, the flap 15 can be relatively stiff, such that it resists bending except about a line of juncture with sanitary napkin 10 corresponding to path of the leg elastics 36 of the undergarment 39.

Figure 21:
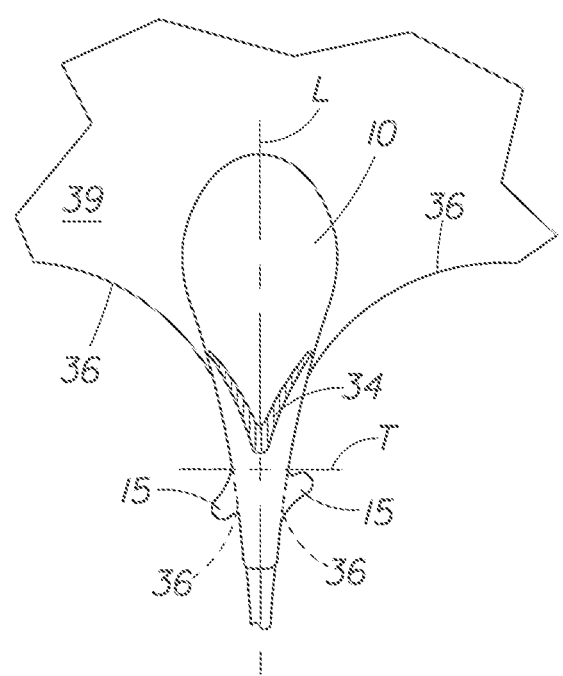

An example of a sanitary napkin (or pantiliner) that is neither symmetric about the longitudinal axis nor the lateral axis is shown in FIG. 21. FIG. 21 shows a sanitary napkin 10 designed for, and being worn in the crotch portion of a so-called thong, or string panty. The very narrow crotch width requires flaps 15, if used to be offset with respect to one another so as to avoid overlapping. As shown, an indicator mark 34, in this case a printed, colored, stylized "V" can indicate proper placement and positioning with respect to the forward leg elastics 36.

Many variations on the above-described indicator markers are contemplated. For example, indicator markers can comprise sensory perception agents, such as menthol lactate in a sufficient amount so as to give the user a feeling of cooling refreshment when the sanitary napkin is properly placed and worn. The indicator markers can be made such that, rather than printing with ink, a material is modified so as to have a different reflective index, or even be transparent, in the region intended to be a indicator marker. Likewise, instead of ink, color can be added by adding colored material in appropriate places, the colored material being additional film, nonwovens, or adhesives, including glue and hot melt adhesives. Such color can be added in or on any component of the sanitary napkin, as long as they are visible to the user when she is positioning the sanitary napkin in her undergarment.

In one embodiment a disposable absorbent article of the present invention can be packaged either singly or in a package with other like articles. The package can be labeled as to the size of undergarment(s) the articles are intended to fit, as well as instructions for use, i.e., a method of properly placing and positioning the absorbent article into the undergarment.

A sanitary napkin of the present invention can be used by following the method herein described. First, if there is a choice of sanitary napkins differentiated by intended undergarment size, the user can choose the sanitary napkin for the size undergarment she wears.

It is preferred that the user place the sanitary napkin into her undergarment while the undergarment is being worn, but pulled down about her legs such that the crotch portion thereof is visible and accessible. The user can then remove one sanitary napkin from the packaging, including any individual wrappers, if any. If the sanitary napkin is provided with pressure sensitive adhesive attachment means, the user can remove any backing strips, release paper, or other covering to expose the adhesive.

Once the sanitary napkin is unwrapped, unfolded, or otherwise prepared for placement, the user can observe (or feel, if tactile) the indicator mark(s) provided thereon and visible (or felt) from the body-facing surface thereof, and place the sanitary napkin in her undergarment while spreading the crotch portion thereof with her legs and visibly lining up the indicator mark(s) with the crotch portion of the undergarment, for example, by lining up the indicator mark(s) with at least one leg elastic, and preferably at least two leg elastics at the location where the leg elastics meet or go under the sanitary napkin. Since the leg elastics are stretched while the user is performing the placement, the indicator markers of the sanitary napkin can be designed for the orientation of the leg elastics during placement, rather than during wear.

Placement can be achieved by known methods, such as by exposing (such as by removing a release paper) pressure sensitive adhesive on the garment-facing side of the sanitary napkin, and pressing the sanitary napkin into the crotch portion of her undergarment.

After placement, the user can check for proper positioning, and, if necessary, remove and replace the sanitary napkin for better alignment of the indicator mark(s) with the crotch portion of the undergarment. This step can be repeated as necessary.

If the sanitary napkin is provided with flaps, the user can then fold the flaps down and under the crotch portion of the undergarment, and, if provided for, affix the flaps to the undergarment by means provided, such as by adhesive attachment means.

The user can then pull up her undergarment, assured that the sanitary napkin is properly placed for optimal functioning in maximizing absorbency while minimizing garment soiling.

To aid the user in properly positioning absorbent articles such as a sanitary napkins having indicator markers, that is, to aid the user in using the indicator markers as a fit guide, the sanitary napkin can be provided with instructions for use. Instructions for use can be provided on or in the packaging in which the sanitary napkin is sold, on related advertising or display media, or on the sanitary napkin itself. The instructions can be printed on packaging, such as on an outside surface thereof, or on a separate paper placed inside the packaging. A package can comprise a plurality of absorbent articles, and each absorbent article can be individually wrapped or packaged, as is commonly known in the art. Instructions for use can include indicia such as text and pictorial diagrams. The printed instructions can include instructions for choosing an absorbent article of the present invention based on the size of the user's undergarment.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal centerline and adapted to be worn in an undergarment having a crotch portion bounded on opposite sides by portions of curved leg openings, said absorbent article comprising a main body portion, said main body portion comprising a liquid pervious body-facing surface, a liquid impervious garment-facing surface, and an absorbent core positioned between said body-facing surface and said garment-facing surface, said absorbent article comprising:
   a. at least two indicator markers, one marker disposed in each of two regions of said absorbent article, wherein at least one of the two indicator markers is visible from said body-facing surface, wherein at least one of the two indicator markers is disposed to indicate proper alignment of said absorbent article with respect to said curved leg openings, and wherein each said indicator marker has a ratio of length to width of at least 1.5 and is oriented at an angle of less than 45 degrees from said longitudinal centerline.

2. The absorbent article of claim 1, wherein said absorbent article is a feminine hygiene article and said indicator marker is chosen from the group consisting of printed marks, colored marks, visible indicia, visible line segments, tactile regions, folds, pleats, notches, debossments, embossments and combinations thereof.

3. The absorbent article of claim 1, wherein said curved leg openings comprise leg elastic material, and said indicator marker indicates said proper alignment by indicating placement of said article with respect to said leg elastic material.

4. The absorbent article of claim 1, wherein said undergarment comprises at least one sewn seam, and said indicator marker indicates said proper alignment by indicating placement of said article with respect to said sewn seam.

5. The absorbent article of claim 2, wherein said absorbent article comprises four indicator markers, one of said four indicator markers being disposed in each of four regions of said absorbent article, said four regions being regions of alignment of each said indicator marker with said portions of a leg opening when the absorbent article is properly placed in an undergarment, and wherein each said indicator marker comprises a plurality of generally linear marks, each said generally linear mark having a ratio of length to width of at least 1.5 and oriented at an angle of less than 45 degrees from said longitudinal centerline.

6. The absorbent article of claim 2, wherein said absorbent article comprises four indicator markers, one of said four indicator markers being disposed in each of four regions of said absorbent article, said four regions being regions of alignment of each said indicator marker with said portions of a leg opening when the absorbent article is properly placed in an undergarment, and wherein each said indicator marker comprises a plurality of generally linear embossments, each said generally linear embossment having a ratio of length to width of at least 1.5 and oriented at an angle of less than 45 degrees from said longitudinal centerline.

7. The absorbent article of claim 1, wherein said absorbent article comprises a transverse centerline perpendicular to said longitudinal centerline, and wherein said absorbent article is not symmetric about either said longitudinal or said transverse centerline.

8. The absorbent article of claim 1, wherein said indicator marks comprise substantially linear marks that are oriented at angles with respect to said longitudinal centerline, said angles being greater in proportion to an increased distance measured laterally outward from said longitudinal centerline.

9. An absorbent article having a longitudinal centerline and adapted to be worn in an undergarment having a crotch portion bounded on opposite sides by portions of curved leg openings, said absorbent article comprising a main body portion, said main body portion comprising a liquid pervious body-facing surface, a liquid impervious garment facing surface, and an absorbent core positioned between said body-facing surface and said garment-facing surface, said absorbent article comprising:
   a. first and second flaps, said flaps extending laterally outwardly from longitudinal edges of said absorbent article, each said flap being adapted to be folded over one of said portions of curved leg openings; and
   b. at least two indicator markers, one marker disposed in each of two regions of said absorbent article, wherein at least one of the two indicator markers is visible from said body-facing surface, said two regions comprising at least a portion of said flaps of said absorbent article, wherein at least one of the two indicator markers is disposed to indicate proper alignment of said absorbent article with respect to said curved leg openings, and wherein each said indicator marker has a ratio of length to width of at least 1.5 and is oriented at an angle of less than 45 degrees from said longitudinal centerline.

10. The absorbent article of claim 9, wherein said indicator marker is chosen from the group consisting of printed marks, colored marks, visible indicia, visible line segments, tactile regions, folds, pleats, notches, debossments, embossments and combinations thereof.

11. The absorbent article of claim 10, wherein said printed mark comprises a plurality of line segments.

12. The absorbent article of claim 9, wherein said indicator marker comprises additional material chosen from the group consisting of nonwoven material, film material, adhesive, ink, colorants, and combinations thereof.

13. The absorbent article of claim 9, wherein said absorbent article comprises a transverse centerline perpendicular to said longitudinal centerline, wherein said absorbent article is not symmetric about either said longitudinal or said transverse centerline.

14. The absorbent article of claim 9, wherein said curved leg openings comprise leg elastic material, and said indicator marker indicates said proper alignment by indicating placement of said article with respect to said leg elastic material.

15. The absorbent article of claim 9, wherein said undergarment comprises at least one sewn seam, and said indicator marker indicates said proper alignment by indicating placement of said article with respect to said sewn seam.

16. The absorbent article of claim 9, wherein said indicator mark comprises linear marks being oriented at angles with respect to said longitudinal centerline, said angles being greater in proportion to an increased distance measured laterally outward from said longitudinal centerline.

17. The absorbent article of claim 9, wherein said absorbent article comprises a transverse centerline perpendicular to said longitudinal centerline, and wherein said absorbent article is not symmetric about either said longitudinal or said transverse centerline.

18. An absorbent article having a longitudinal centerline and a transverse centerline perpendicular to said longitudinal centerline, wherein said absorbent article is not symmetric about said transverse centerline, said absorbent article adapted to be worn in an undergarment having a crotch portion bounded on opposite sides by portions of curved leg openings, said absorbent article comprising a main body portion, said main body portion comprising a liquid pervious body-facing surface, a liquid impervious garment facing surface, and an absorbent core positioned between said body-facing surface and said garment-facing surface, said absorbent article further comprising:
   a. first and second flaps, said flaps extending laterally outwardly from longitudinal edges of said absorbent article, each said flap being adapted to be folded over one of said portions of curved leg openings;
   b. at least one indicator marker visible from said body-facing surface, said indicator markers disposed to indicate proper alignment of said absorbent article with respect to said curved leg openings, said indicator marker having a ratio of length to width of at least about 1.5 and being oriented at an angle from the longitudinal axis of between about 10 degrees and about 30 degrees.

19. An absorbent article having a longitudinal centerline and adapted to be worn in an undergarment having a crotch portion bounded on opposite sides by portions of curved leg openings, said absorbent article comprising a main body portion, said main body portion comprising a liquid pervious body-facing surface, a liquid impervious garment-facing surface, and an absorbent core positioned between said body-facing surface and said garment-facing surface, said absorbent article comprising:
   a. at least one indicator marker visible from said body-facing surface, said indicator marker disposed to indicate proper alignment of said absorbent article with respect to said curved leg openings;
   wherein said indicator marker comprises substantially linear marks that are oriented at angles with respect to said longitudinal centerline, said angles being greater in proportion to an increased distance measured laterally outward from said longitudinal centerline.

20. An absorbent article having a longitudinal centerline and adapted to be worn in an undergarment having a crotch portion bounded on opposite sides by portions of curved leg openings, said absorbent article comprising a main body portion, said main body portion comprising a liquid pervious body-facing surface, a liquid impervious garment facing surface, and an absorbent core positioned between said body-facing surface and said garment-facing surface, said absorbent article comprising:
- a. first and second flaps, said flaps extending laterally outwardly from longitudinal edges of said absorbent article, each said flap being adapted to be folded over one of said portions of curved leg openings; and
- b. at least one indicator marker visible from said body-facing surface, said indicator markers disposed to indicate proper alignment of said absorbent article with respect to said curved leg openings;

wherein said indicator marker comprises linear marks being oriented at angles with respect to said longitudinal centerline, said angles being greater in proportion to an increased distance measured laterally outward from said longitudinal centerline.

\* \* \* \* \*